US 6,526,355 B1

(12) United States Patent
Ni et al.

(10) Patent No.: US 6,526,355 B1
(45) Date of Patent: Feb. 25, 2003

(54) INTEGRATED FULL WAVELENGTH SPECTROMETER FOR WAFER PROCESSING

(75) Inventors: Tuqiang Ni, Fremont, CA (US); Tuan Ngo, Milpitas, CA (US); Chung-Ho Huang, Fremont, CA (US); Andrew Lui, Fremont, CA (US); Farro Kaveh, Palo Alto, CA (US)

(73) Assignee: Lam Research Corporation, Fremont, CA (US)

( * ) Notice: Subject to any disclaimer, the term of this patent is extended or adjusted under 35 U.S.C. 154(b) by 0 days.

(21) Appl. No.: 09/539,312

(22) Filed: Mar. 30, 2000

(51) Int. Cl.[7] ............................................. G06F 19/00
(52) U.S. Cl. ..................... 702/32; 702/31; 315/111.21
(58) Field of Search ................ 702/32, 31; 315/111.21

(56) References Cited

U.S. PATENT DOCUMENTS

| 4,267,572 | A | | 5/1981 | Witte ........................ 364/498 |
| 4,365,303 | A | | 12/1982 | Hannah et al. ............. 364/498 |
| 4,490,806 | A | * | 12/1984 | Enke et al. ................. 708/445 |
| 5,347,460 | A | | 9/1994 | Gifford et al. .............. 364/468 |
| 5,403,621 | A | * | 4/1995 | Jackson et al. ........ 427/255.23 |
| 5,450,205 | A | * | 9/1995 | Sawin et al. ................. 216/60 |
| 5,546,322 | A | * | 8/1996 | Gifford et al. .............. 702/100 |
| 5,664,066 | A | * | 9/1997 | Sun et al. ..................... 706/25 |
| 5,715,051 | A | * | 2/1998 | Luster ..................... 356/237.2 |
| 5,757,483 | A | * | 5/1998 | Pierce, III ................... 356/305 |
| 5,846,373 | A | | 12/1998 | Pirkle et al. ................ 156/345 |
| 6,077,386 | A | | 6/2000 | Smith, Jr. et al. ........... 156/345 |
| 6,090,302 | A | | 7/2000 | Smith, Jr. et al. ............. 216/60 |
| 6,091,749 | A | * | 7/2000 | Hoffmaster et al. .......... 372/25 |
| 6,157,867 | A | | 12/2000 | Hwang et al. ............... 700/121 |
| 6,243,738 | B1 | * | 6/2001 | Hayles et al. ............... 370/312 |
| 6,265,831 | B1 | * | 7/2001 | Howald et al. ........ 118/723 AN |

FOREIGN PATENT DOCUMENTS

EP 0677737 A2 10/1995 .......... G01N/21/71

OTHER PUBLICATIONS

U.S. patent application No. 09/539,313, filed Mar. 30, 2000, entitled: "Plug and Play Sensor Integration for a Process Module".

* cited by examiner

Primary Examiner—John S. Hilten
Assistant Examiner—Stephen J. Cherry
(74) Attorney, Agent, or Firm—Beyer Weaver & Thomas, LLP

(57) ABSTRACT

A process chamber with a computer system that controls the process chamber is connected to one or more spectrometers. The spectrometers may be part of an interferometer or may be an optical emission spectrometer. The spectrometers may be CCD or photodiode arrays of 2,048 elements. An input board forms part of the computer system and is directly connected to the spectrometers. The input board provides data from the spectrometers to dual port memory, which is directly accessible to the CPU of the computer system. The use of a state machine and adder on the input board allows computation and placement of the data from the spectrometers on to the dual port memory, so that the CPU is not needed for such placement.

6 Claims, 4 Drawing Sheets

INTEGRATED FULL WAVELENGTH SPECTROMETER FOR WAFER PROCESSING

RELATED APPLICATIONS

This application is related to the commonly assigned application Ser. No. 09/539,313 entitled "PLUG AND PLAY SENSOR INTEGRATION FOR A PROCESS MODULE" filed on even date herewith and incorporated herein by reference.

BACKGROUND OF THE INVENTION

The present invention relates to the processing devices. More particularly, the present invention relates to the use of spectrometers in semiconductor processing devices.

In the manufacturing processes, which use a plasma in a plasma chamber, monitoring the process within the plasma chamber is desirable.

To facilitate discussion, FIG. 1 is a schematic illustration of a prior art plasma processing device 10 and spectrometer 12. The plasma processing device 10 may comprise a plasma processing chamber 14 and a device computer 16. The spectrometer 12 may be controlled by a spectrometer computer 17. The spectrometer computer 17 may be linked to the device computer 16 by a serial connection 18, such as an RS-232 connection, which may have a communications speed of 9600 bytes per second. The plasma processing chamber 14 may support a power source 19. The spectrometer 12 may comprise a diffraction grating 22 and a one dimensional charge coupled device (CCD) array 23. The array may have between 1,000-3,000 elements.

Since the spectrometer 12 is controlled by a spectrometer computer 17 that is linked to the device computer 16 by a serial connection 18, it may be difficult to get large amounts of data provided by the 1000-3000 elements of the CCD array at a scan rate on the order of 200 scans per seconds to the device computer 16 in real time so that the device computer 16 can analyze the data and control the process in the plasma process chamber 14. Therefore, in the prior art, the data from the spectrometer may be reduced by the spectrometer computer 17. The reduced data may then be transmitted to the device computer 16. In addition, the spectrometer computer 17 may need to be programmed individually from the device computer 16 increasing the set up time. For example, to reduce data size, the spectrometer computer 17 may be programmed to only transfer data regarding a narrow spectrum. The device computer 16 would also need to be programmed to accommodate data from the narrow spectrum. To program the spectrometer computer 17, the spectrometer computer 17 may require its own input and output hardware, such as a display and keyboard, which increases the cost and footprint of the overall hardware. In addition, the transfer of data between the spectrometer computer 17 and the device computer 16 may take CPU time of the device computer 16.

In view of the foregoing, it is desirable to provide a plasma processing device with a spectrometer that is able to receive and process large amounts of data from the spectrometer in real time, to allow real time control of the plasma processing device as a result of the large amounts of data from the spectrometer.

SUMMARY OF THE INVENTION

The invention relates, in one embodiment, to a plasma processing device, comprising: a plasma processing chamber; a computer connected to the plasma processing device, comprising: a first CPU; a CPU bus connected to the first CPU; and a first input board connected to the CPU bus; and a spectrometer connected to the input board.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

The present invention will now be described in detail with reference to a few preferred embodiments thereof, as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

Figure 1:
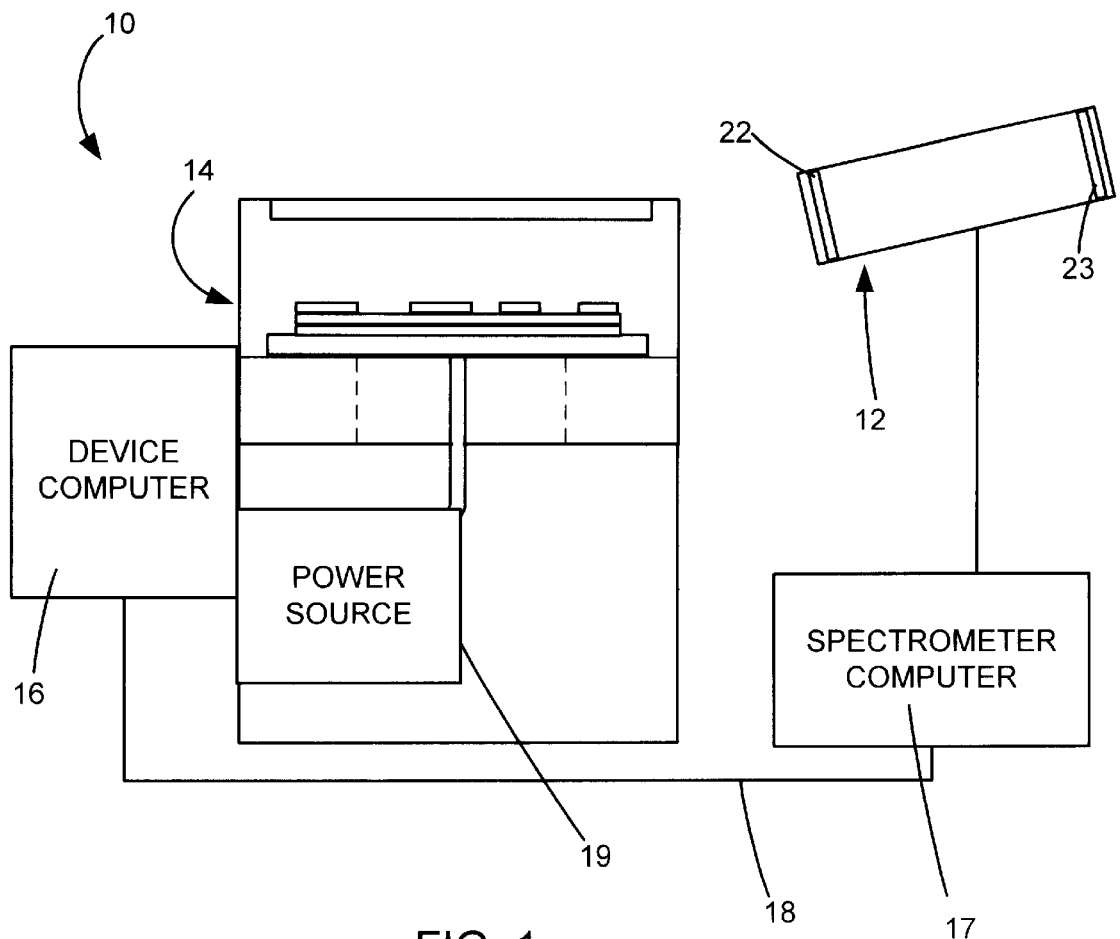
FIG. 1 is a schematic view of a prior art plasma processing device.
Figure 2:
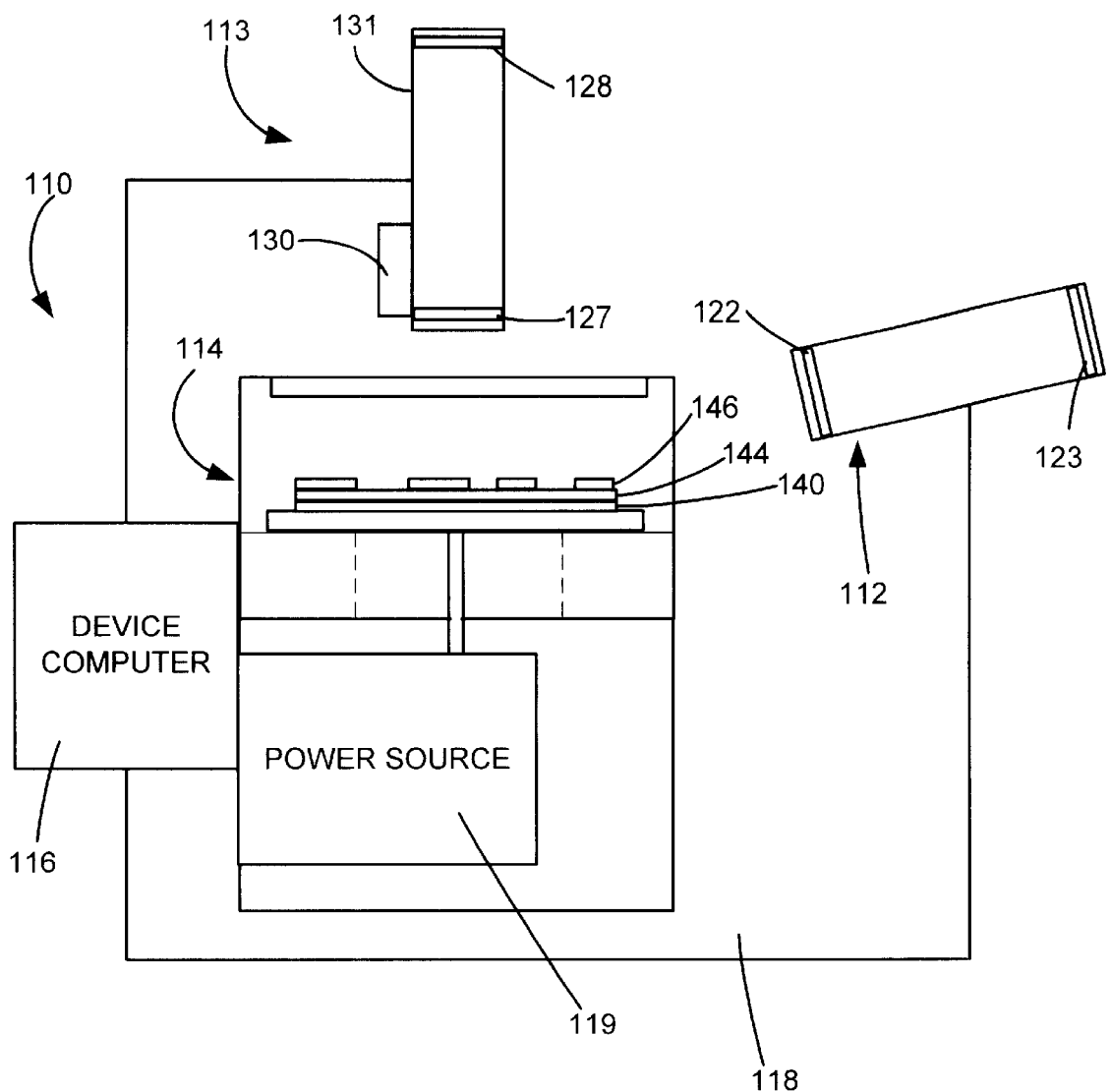
FIG. 2 is a schematic view of a plasma processing device used in a preferred embodiment of the invention.

To facilitate discussion, FIG. 2 is a schematic illustration of a preferred embodiment of a plasma processing device 110, an interferometer 113, and an optical emission spectrometer 112. The plasma processing device 110 comprises a plasma processing chamber 114 and a device computer 116. The interferometer 113 and the optical emission spectrometer 112 are integrally connected to the device computer 116. The plasma processing chamber 114 supports a power source 119. The interferometer 113 may comprise a light source 130, and a spectrometer 131 comprising a diffraction grating 127 and a one dimensional charge coupled device (CCD) array 128. In another embodiment, the spectrometer may be another prism device and a photodiode array. In another embodiment a two dimensional CCD array may be used. The arrays may have between 1,000-3,000 photosensitive elements (such as photodiode or CCD elements). The optical emission spectrometer 112 may comprise a diffraction grating 122 and a one or two-dimensional charge coupled device (CCD) array 123. The interferometer 113 is positioned directly above the plasma processing chamber 114 and the optical emission spectrometer 112 is positioned on a side of the plasma processing chamber 114 in a preferred embodiment of the invention.

Figure 3:
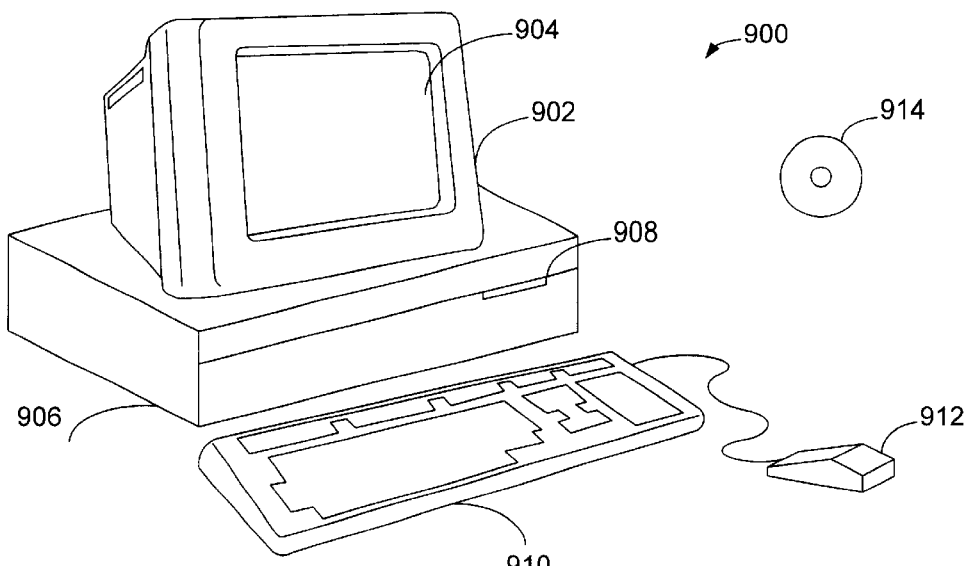
FIG. 3 is a view of a computer system which may be used in a preferred embodiment of the invention.
Figure 4:
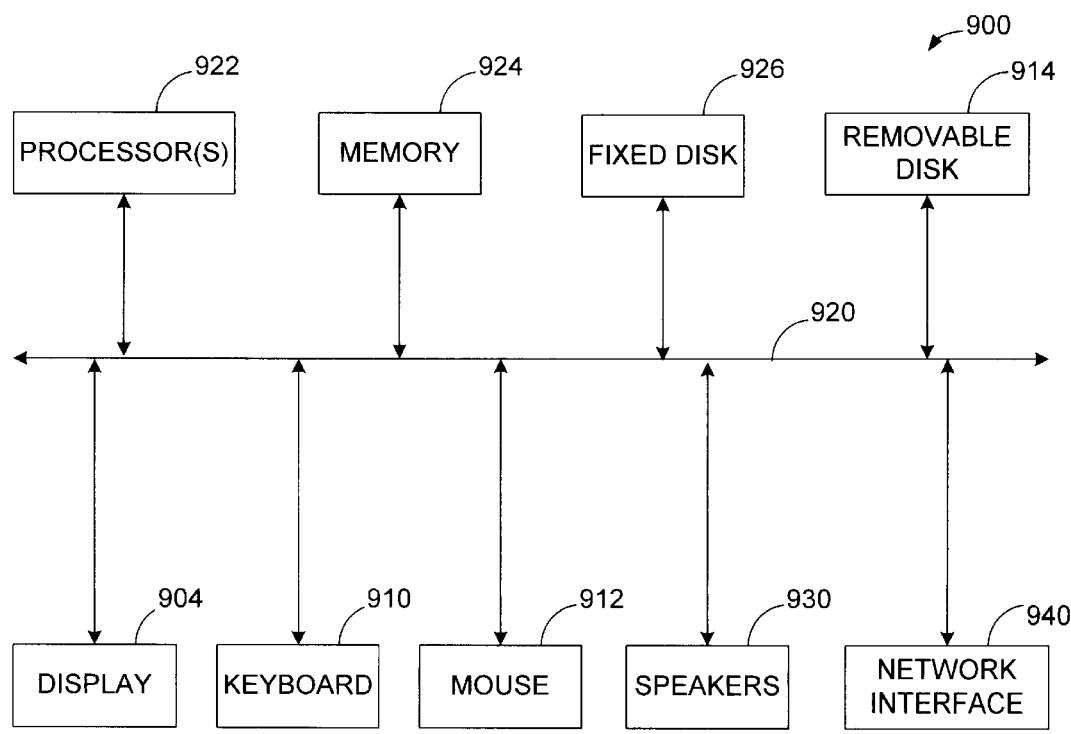
FIG. 4 is a block diagram of the computer system shown in FIG. 3.

FIGS. 3 and 4 illustrate a computer system 900, which is suitable for the device computer 116 on various embodiments of the present invention. FIG. 3 shows one possible physical form of the computer system. Of course, the computer system may have many physical forms ranging from an integrated circuit, a printed circuit board, and a small handheld device up to a huge super computer. Computer system 900 includes a monitor 902, a display 904, a housing 906, a disk drive 908, a keyboard 910, and a mouse 912. Disk 914 is a computer-readable medium used to transfer data to and from computer system 900.

FIG. 4 is an example of a block diagram for computer system 900. Attached to system bus 920 are a wide variety of subsystems. Processor(s) 922 (also referred to as central processing units, or CPUs) are coupled to storage devices including memory 924. Memory 924 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable type of the computer-readable media described below. A fixed disk 926 is also coupled bi-directionally to CPU 922; it provides additional data storage capacity and may also include any of the computer-readable media described below. Fixed disk 926 may be used to store programs, data, and the like and is typically a secondary storage medium (such as a hard disk) that is slower than primary storage. It will be appreciated that the information retained within fixed disk 926, may, in appropriate cases, be incorporated in standard fashion as virtual memory in memory 924. Removable disk 914 may take the form of any of the computer-readable media described below.

CPU 922 is also coupled to a variety of input/output devices such as display 904, keyboard 910, mouse 912 and speakers 930. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 922 optionally may be coupled to another computer or telecommunications network using network interface 940. With such a network interface, it is contemplated that the CPU might receive information from the network, or might output information to the network in the course of performing the above-described method steps. Furthermore, method embodiments of the present invention may execute solely upon CPU 922 or may execute over a network such as the Internet in conjunction with a remote CPU that shares a portion of the processing.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs), and ROM and RAM devices.

Figure 5:
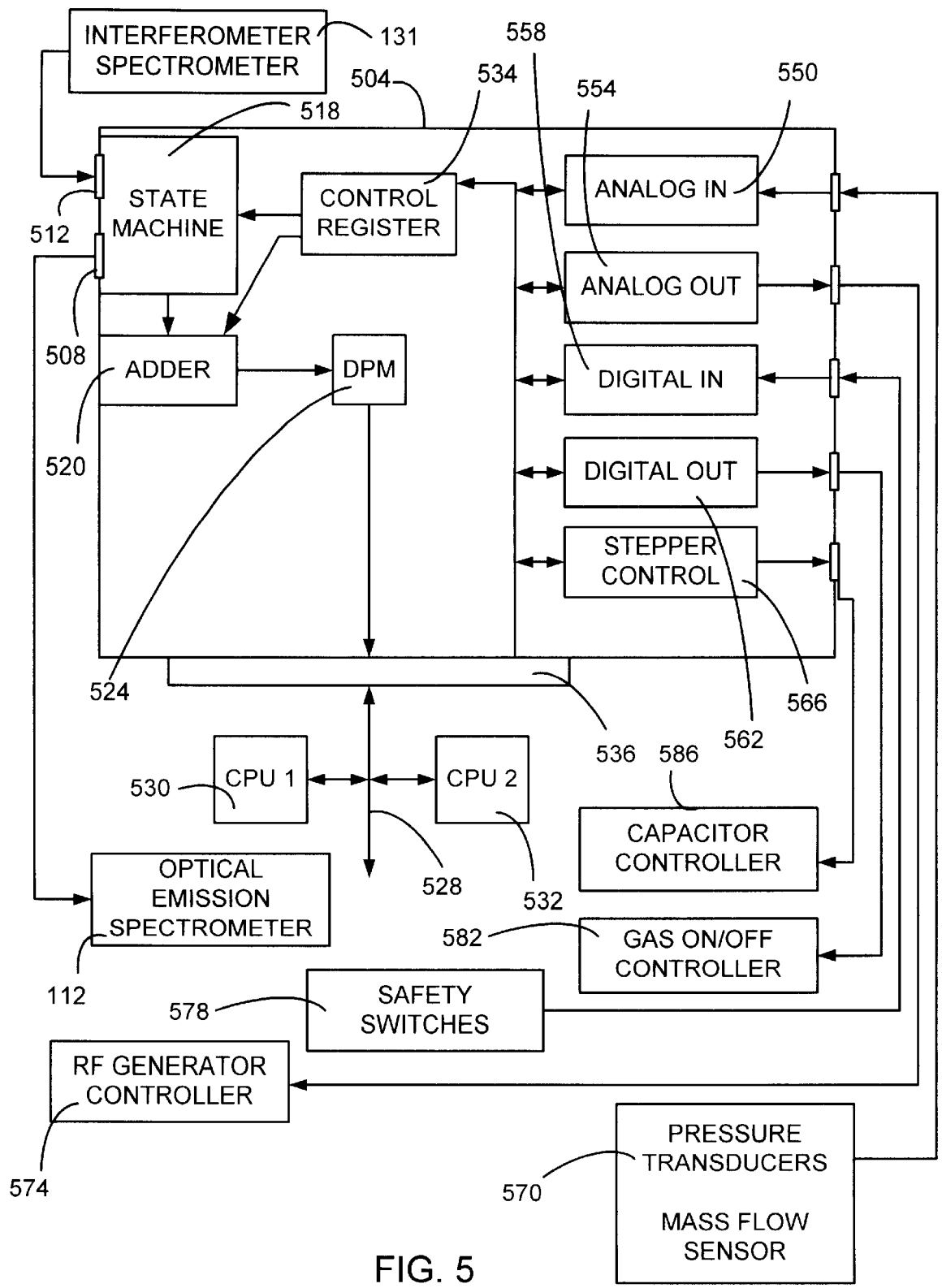
FIG. 5 is a schematic view of an input board used in a preferred embodiment of the invention.

FIG. 5 is a more detailed schematic illustration of an input board 504 of the device computer 116. In a preferred embodiment of the invention, the input board 504 is a VME bus board. The input board 504 has a first input 512 for a connection to the spectrometer 131 of the interferometer 113 and a second input 508 for a connection to the optical emission spectrometer 112. The first and second inputs 512, 508 are connected to a state machine 518, which is a timing generator analog to digital converter, which controls the exposure time and scan rate of the spectrometers. The state machine 518 synchronizes the data from the interferometer spectrometer 131 and optical emission spectrometer 112 through the first and second inputs 512, 508 and digitizes the data. The data is then passed to an adder circuit 520. The adder 520 is able to sum together 1 to 16 spectrums pixel by pixel. The data from the adder 520 is stored on a dual port memory (DPM) 524. The dual port memory 524 is concurrently accessible by the adder circuit 520 and a CPU bus 528, which connects the dual port memory 524 with a first CPU 530 and a second CPU 532. The CPU bus 528 is connected to the dual port memory 524 through the input board connector 536. The CPU bus 528 is also connected to a control register 534 through the input board connector 536. The control register 534 provides control input to the state machine 518 and the adder 520. In the preferred embodiment of the invention, the input board connector 536 is a VME bus board connector.

In the preferred embodiment of the invention, an analog input 550, an analog output 554, a digital input 558, a digital output 562, and a stepper control 566 are all supported on the input board 504. The analog input 550, analog output 554, digital input 558, digital output 562 and stepper control 566 receive input from the CPU bus 528 and provide output to the control register 534 and the CPU bus 528. The analog input 550 is aconnected to and receives analog input from analog sensors such as pressure transducers and mass flow sensors 570. Analog sensors provide measurements of various amplitudes, instead of digital data with two states. The analog output is connected to and provides output to analog controls such as an RF generator controller 574 which requires various amplitudes (i.e., how much RF power), instead of digital data with two states. The digital input 558 is connected to and receives input from digital sensors that provide digital input with only two states (i.e., 1 and 0), such as safety switches 578. The digital output 562 is connected to and provides output to digital controllers, such as gas on and off controller 582, which only have two input states. The stepper control 566 is connected to and provides output to controllers that require stepped outputs such as controllers that rotate capacitors 586 for matching impedance.

In the operation of the invention, a substrate 140 (FIG. 2) is placed in the plasma processing chamber 114. The substrate 140 may be covered with an intermediate layer 144, which may be partially covered by a mask 146. The first and second CPU's 530, 532 (FIG. 5) may send a command over the CPU bus 528 through the input board connector 536 to the digital output 562 to turn on the gas controller 582 to provide a gas to the plasma processing chamber 114. The pressure transducers and mass flow sensor 570 provide signals to the analog input 550. The data from the analog input 550 is sent to the first and second CPU's 530, 532. If all safety features are operative, the safety switches 578 may be set so that no signal is sent to the digital input 558, so that no signal is sent from the digital input 558 to the first and second CPU's 530, 532 allowing the plasma process to proceed. In an alternative embodiment, the safety switches 578 may be set so that a signal is required from the safety switches to the digital input 558 to allow the process to proceed.

The first and second CPU's 530, 532 provide a signal through the CPU bus 528 and through the input board connector 536 to the analog output 554 to the RF generator controller 574 to cause the RF generator to provide an RF signal of a specified amplitude. The first and second CPU's 530, 532 also provide a signal through the CPU bus 528 and through the input board connector 536 to the stepper control 566, which sends a signal to the capacitor controller 586 to adjust the capacitor. The RF generator and the adjustment of the capacitor in a match network energizes the gas to create a plasma.

The optical emission spectrometer 112 may measure light produced by the plasma. In the preferred embodiment of the invention, the optical emission spectrometer 112 has 2048 CCD elements with each element generating two bytes of data. In the preferred embodiment the scan rate of the optical emission spectrometer 112 is about 10 to 200 scans per second. More preferably the scan rate is greater than 80 scans per second. The 4,096 bytes of data from the optical emission spectrometer 112 pass through the second input 508 to the state machine 518. At the beginning of the process, detailed data may be desired, so the first and second CPU's 530, 532 may send a signal through the CPU bus 528 and the input board connector 536 to the control register 534, which may signal the adder 520 to not sum any of the spectrums together, but to allow each spectrum n=1 of 4,096 bytes to pass to the DPM 524. The state machine 518 receives the 4,096 bytes spectrum from the optical emission spectrometer 112 and passes the 4,096 bytes of data to the adder 520. The adder 520 takes the single spectrum of 4,096 bytes and since the control register has set n=1, passes the 4,096 bytes of data to the dual port memory 524 with each scan. By setting n=1, the greatest amount of data is provided with the greatest amount of noise. The first and second CPU's are able to use the data in the DPM 524 and from the analog iniput 550 and the digital input 558 to provide control signals to the analog output 554, digital output 562, and stepper control 566. The spectrum from the optical emission spectrometer 112 may be used to indicate the presence or absence of chemical species in the plasma or on the substrate 140.

When the plasma is generated and stabilized, parts of the intermediate layer 144 not covered by the mask 146 are etched. The device computer 116 may be programmed to require less frequent data from the optical emission spectrometer 112, so that the control register 534 sends a message to the adder 520 to set n=16. As a result, the adder 520 sums 16 of the 4,096 byte spectrums together, resulting in less frequent data with less noise, since the summing of the spectrums has the effect of averaging the spectrums together. Therefore, on the order of 4,096 bytes of data are passed from the adder 520 to the DPM 524 every 16 scans. The interferometer 113 is used to measure the etch rate of the intermediate layer 144. This may be achieved by measuring the intensity of reflected light generated by the light source 130, some of which passes through the intermediate layer 144 causing constructive and destructive interference. To limit the amount of noise, the control register 534 may send a message to the adder 520 to set n=16. In this case, 16 spectrums from the interferometer 113 are summed together and then stored in the DPM 524. The first and second CPU's 530, 532 may access data only for a single wavelength of the spectrum to measure the change in thickness of the intermediate layer 144 or may access data from multiple wavelengths and perform a calculation to determine the thickness of the intermediate layer 144.

If the first and second CPU's 530, 532 calculate that the change in thickness of the intermediate layer 144 is less than a set threshold, or the thickness of the intermediate layer 144 is greater than a set threshold, the first and second CPU's 530, 532 signal through the input board 504 for the plasma process device 110 to continue the etching process. This may be done by having the digital output 562 signal the gas on/off controller 582 to continue to provide a gas and the analog output 554 signal the RF generator controller 574 to continue to provide an RF output, which is sufficient to energize the gas to a plasma. In addition, the stepper control 566 continues to provide signals to the capacitor controller 586 to match impedance.

If the first and second CPU's 530, 532 calculate that the change in thickness of the intermediate layer 144 is greater than or equal to a set threshold, or the thickness of the intermediate layer 144 is less than or equal to a set threshold, the first and second CPU's 530, 532 signal through the input board 504 for the plasma processing device 110 to discontinue the etching process. This may be done by having the digital output 562 signal the gas on/off controller 582 to discontinue providing gas or by having the analog output 554 signal the RF generator controller 574 to discontinue the RF output.

In the alternative, the data from the optical emission spectrometer 112 may be analyzed by the first and second CPU's 530, 532 to detect the presence of silicon chlorine ($SiCl_2$) in the plasma. The presence of silicon chlorine may be used to indicate that the intermediate layer 144 has been etched through to a silicon layer, to allow the resulting silicon chlorine.

In this example, the interferometer 113 and the optical emission spectrometer 112 are integrated with the device computer 116 to allow the device computer 116 to analyze the data from the interferometer 113 and the optical emission spectrometer 112 and use the data to control the plasma processing device 110. The integration allows data from the spectrometers to be placed in memory in real time, where the memory is accessible to the CPU, but the placement of the data into memory requires little CPU time.

While this invention has been described in terms of several preferred embodiments, there are alterations, permutations, and equivalents which fall within the scope of this invention. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

What is claimed is:

1. A plasma processing device, comprising:
   a plasma processing chamber;
   a gas source;
   a plasma power source;
   a computer connected to the plasma processing device, comprising:
      a first CPU;
      a CPU bus connected to the first CPU;
      a first board connected to the CPU bus, comprising at least one controllable connection between the CPU bus and the gas source and the plasma power source, wherein the first board further comprises:
         a first input port connected to the first spectrometer;
         a state machine connected to the first input port;
         an adder connected to the state machine;
         dual port memory connected between the adder and the CPU bus;
         a control register connected to the CPU bus, state machine, and the adder;
         an analog input connected to the control register and the CPU bus;

a digital input connected to the control register and the CPU bus; and wherein the at least one controllable connection, comprises:

an analog output connected to the control register and the CPU bus;

a digital output connected to the control register and the CPU bus; and a stepper control connected to the control register and the CPU bus;

a first spectrometer connected to the first board;

a plurality of safety switches electrically connected to the digital input;

a gas on/off controller electrically connected to the digital output;

an RF generator controller electrically connected to the analog output;

a pressure transducer electrically connected to the analog input; and a capacitor controller electrically connected to the stepper control.

2. The plasma processing device, as recited in claim 1, wherein the first spectrometer comprises an array with greater than 1,000 photosensitive elements.

3. The plasma processing device, as recited in claim 1, wherein the first spectrometer comprises a CCD array with greater than 2,000 elements.

4. A method of manufacturing, comprising the steps of:

providing a signal from a CPU of a device computer through a digital output to a gas controller to signal the gas controller to allow a flow of gas into a plasma processing chamber;

providing a signal from the CPU of the device computer through an analog output to an RF generator control to signal the RF generator control to cause an RF generator to provide an RF signal to generate a plasma in the plasma processing chamber;

passing light from the plasma processing chamber to an array of photosensitive elements;

collecting data from the array of photosensitive elements;

passing the data from the array of photosensitive elements to a state machine on an input board of the device computer;

passing the data from the state machine to an adder on the input board;

summing at least one spectrum of the data in the adder; and passing the summed spectrum to a dual port memory.

5. The method, as recited in claim 4, further comprising the steps of:

passing data from the dual port memory to the CPU;

processing the data passed from the dual port memory; and transmitting signals from the CPU to the digital output and the analog output based on the processed data from the dual port memory.

6. The method, as recited in claim 3, wherein the passing of data from the array of photosensitive elements occurs at a rate of more than 100 times a second, and wherein the array of photosensitive elements has greater than 1,000 elements.

* * * * *